United States Patent [19]
Bowen et al.

[11] 3,935,468
[45] Jan. 27, 1976

[54] LIGHT RESPONSIVE DETECTOR

[75] Inventors: Howard Bowen, Wilmette; Frederick W. Spinner, Elk Grove Village, both of Ill.

[73] Assignee: Research Technology Incorporated, Skokie, Ill.

[22] Filed: Sept. 11, 1974

[21] Appl. No.: 504,980

[52] U.S. Cl. ............... 250/572; 250/562; 356/237; 73/157
[51] Int. Cl.² .......................................... G01N 21/30
[58] Field of Search ...... 73/157; 250/562, 563, 572, 250/229; 356/200, 237, 238; 340/280

[56] References Cited
UNITED STATES PATENTS

| | | | |
|---|---|---|---|
| 3,105,152 | 9/1963 | Nash | 250/239 X |
| 3,334,239 | 8/1967 | Nash | 250/229 X |
| 3,406,568 | 10/1968 | Sadowski | 73/157 X |
| 3,501,760 | 3/1970 | Menary | 73/157 X |
| 3,613,444 | 10/1971 | Grunwald et al. | 73/157 |
| 3,783,274 | 1/1974 | Towne et al. | 250/229 X |

*Primary Examiner*—Walter Stolwein
*Attorney, Agent, or Firm*—Hill, Gross, Simpson, Van Santen, Steadman, Chiara & Simpson

[57] ABSTRACT

A film inspection apparatus is provided for detecting changes in surface profile of film, e.g., edge breaks sprocket hole tears, poor splices, etc. The film inspection apparatus includes a device mounted above a sapphire film support and having a pair of cantilever jewel carrying members for feeling the surface profile adjacent each edge of a traveling web of film. Each cantilever includes a thin vane which extends into and modulates a respective light beam which is incident upon a respective photocell. Each photocell is connected to a separate channel of a braking circuit to operate a brake for the film driving mechanism when a surface profile is encountered which is to be considered as an unacceptable flaw.

18 Claims, 6 Drawing Figures

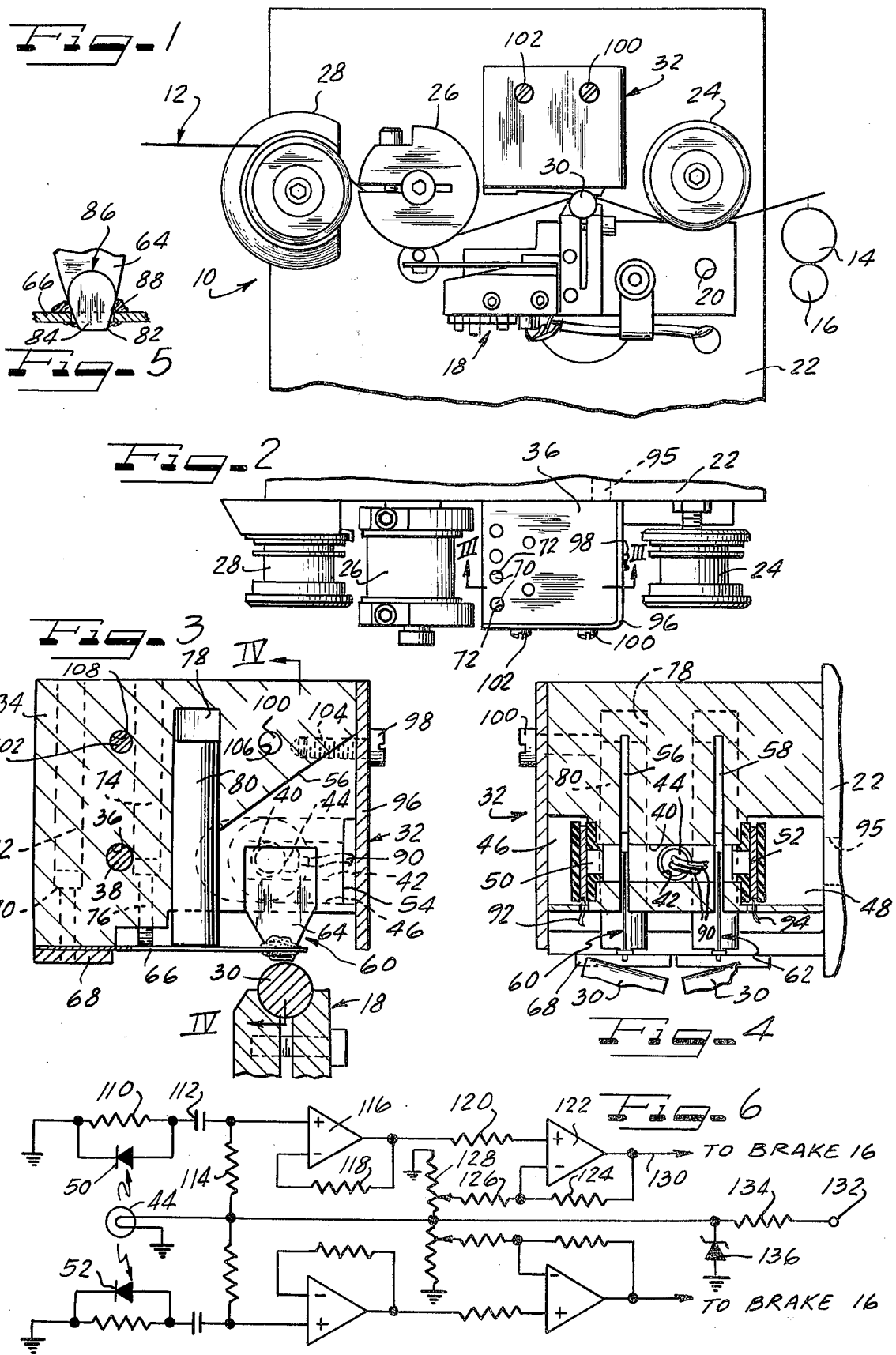

LIGHT RESPONSIVE DETECTOR

BACKGROUND OF THE INVENTION

1. Field of the Invention

This invention relates to film inspection apparatus, and is more particularly concerned with a light modulating device for reading the surface profile of a moving film and stopping the film in response to an unacceptable surface profile.

2. Description of the Prior Art

Various arrangements are known in the art for inspecting films to detect elongated sprocket holes, sprocket run off or punch, edge breaks and poor splices, including Grunwald et al. U.S. Pat. No. 2,699,676; Grunwald et al. U.S. Pat. No. 2,934,949; Grunwald et al. U.S. Pat. No. 3,613,444; Phillimore U.S. Pat. No. 2,469,608; Menary U.S. Pat. No. 3,180,143 and 3,501,760 and Wallace U.S. Pat. No. 3,778,802. These prior art publications disclose various arrangements for detecting unacceptable flaws or defects in film.

As pointed out in the aforementioned Wallace patent, motion picture film usually consist of an elongate strip of material of a thickness of approximately 5 mils which has a picture track consisting of a series of successive pictures or frames occuping a substantial portion of the width of the film, a sound track adjacent the picture track on one edge of the film, and a series of sprocket holes in the opposite edge of the film to receive the sprocket wheels of a projector in order to provide proper indexing of the pictures as the film is shown. Outboard of the sprocket holes, and of course along the opposite edge of the film, the film has a continuous web or track which defines a continuous edge of the film. After a film has been projected, particularly after the film has been projected many times, or after the film has been used on a faulty projector, it tends to acquire defects which will impair future projections. Among these defects are those set forth above which include: elongated sprocket holes, sprocket run off or punch, where the projector sprocket is run out of registry with the sprocket holes and has indented or embossed the film, sprocket holes torn laterally out to the edge of the film and identified as edge breaks, the film splices which are poorly made and occupy an abnormal length along the film, usually in excess of one-eighth inch, and splices made with pins, paper clips or staples, and breaks the film which may have occurred subsequent to the last previous film inspection.

As also pointed out by Wallace, while these prior arrangements have been generally satisfactory in detecting various types of defects in the film, they have been unsuitable for making a suitable inspection when the film is moved past the inspection device at an extremely high rate of speed, in the order of 1,600 feet per minute. Therefore, in the detection of edge breaks the sensitivity of the detector of the prior art arrangements has not been sufficiently sensitive to permit film inspection speeds in the order of 1,600 feet per minute.

Inasmuch as these prior art publications illustrate and teach the driving and braking of the film in an inspection device and as the driving and braking per se do not form a part of the present invention, except in combination with the detection apparatus disclosed herein, these teachings are incorporated herein by reference and detailed description of this apparatus is eliminated herein for purpose of simplicity and clarity.

SUMMARY OF THE INVENTION

It is an object of the present invention to provide a new and improved film inspection device which may operate at speeds higher than heretofore disclosed, particularly at speeds of 2,000 feet per minute.

Another object of the invention is to provide film inspection apparatus of increased sensitivity for detection of the surface profile up to 10 millions of an inch, with the detection sensitivity being adjustable to accommodate film incongruities which may be considered as a defect by one operator but not considered as a defect by another operator.

According to the invention, a film inspection device is mounted above and adjacent to a film support, in the form of sapphire rods, which together define part of a path of a moving film, which path includes a plurality of rollers. The film is moved along this path by a drive mechanism including a motor having a brake.

The film inspection device includes a block having a transverse bore therethrough in which is mounted a lamp. A pair of photocells are mounted at opposite ends of the bore to receive the light beam emanating from the lamp. A pair of slots are provided in the block intermediate the lamp and respective photocells for receiving respective vanes which are mounted on respective cantilevers. Each cantilever carries a jewel disposed above a respective sapphire supporting rod to read the surface profile of the film as its moves between the sapphire rods and the jewels. A pair of vertical bores each receive a metal cylinder which bears upon and damps the movement of the cantilever arms and a pair of vertical bores which receive adjusting screws for adjusting the preloading of the cantilever arms.

Each photocell is connected to a respective channel of a braking circuit and each channel of the braking circuit includes a level setting circuit for setting the response level for braking at the option of the operator.

BRIEF DESCRIPTION OF THE DRAWINGS

Other objects, features and advantages of the invention, its organization, construction and operation will be best understood from the following detailed description of a preferred embodiment of the invention taken in conjunction with the accompanying drawings, on which:

FIG. 1 is a front elevational view of a film inspection apparatus constructed in accordance with the principles of the present invention;

FIG. 2 is a top view of the portion of the apparatus illustrated in FIG. 1;

FIG. 3 is a sectional view of the flaw or defect detector of FIGS. 1 and 2 taken substantially along the line III—III;

FIG. 4 is a sectional view of the defect detector taken substantially along the line IV—IV of FIG. 3;

FIG. 5 is a fragmentary sectional view of a portion of the vane and cantilever arm apparatus illustrated in FIG. 3; and FIG. 6 is a schematic circuit illustration of a braking circuit constructed in accordance with the invention.

DESCRIPTION OF THE PREFERRED EMBODIMENT

Referring to FIGS. 1-4, a film inspection apparatus is generally illustrated at 10 for detecting defects in a film 12 which is moved through the apparatus by a drive mechanism 14 which has a brake 16.

A film supporting apparatus 18 includes a pair of sapphire rods 30 for supporting the underneath side of the film 12 as it passes through the inspection apparatus. The support structure 18 may advantageously be mounted for movement between and unloading and a loading condition about a pivot 20, as described in the Wallace U.S. Pat. No. 3,778,802, and will not be treated in further detail herein. It suffices to say that the film is entrained and guided about a plurality of rollers 24, 26 and 28 mounted on a panel 22, so as to traverse and be supported on the sapphire cylinders 30.

A defect detector 32 is mounted above and adjacent to the sapphire cylinders 30 and includes a block 34, e.g. an aluminum block, having a transverse bore 36 therethrough, preferably counterbored, to receive a machine screw 38 for mounting the block on the panel 22.

The block 34 also includes a transverse bore 40 and a bore 42 which intersects the transverse bore 40. A lamp 44 is mounted in the bore 42 to provide a light beam in both directions through the transverse bore 40 to be received by a pair of photocells 50 and 52 mounted in respective recesses 46 and 48 at the ends of the transverse bore 40. The recesses 46 and 48, a recess 54, a cover plate 96, and the panel 22 serve as a raceway for the leads 90, 92 and 94 of the lamp 44 and the photocells 50 and 52. Advantageously, the panel 22 may include a bore 95 as a conduit for extending electrical connections to the photocells and diodes from a source of power and to the controlled braking circuit.

A pair of slots 56 and 58 extend into the block 34 to intersect the transverse bore 40. A pair of light modulating vanes 60 and 62 extend through respective ones of the slots 56 and 58 and into an interference relationship with the light beam within the transverse bore 40. Inasmuch as these structures are identical, only one will be illustrated with particular reference taken to FIG. 3.

In FIG. 3, the vane mechanism 60 is illustrated as including a vane 64 mounted on a cantilever arm 66 which is secured at one end thereof between the bottom surface of the block 34 and a member 66 by a pair of screws 70 which extend through respective vertical bores 72. A vertical threaded bore 74 is provided forward of the bores 72 for receiving a screw 76 for adjusting the preloading on the cantilever arm 66.

Forward of the vertical bore 76 is another vertical bore 78 which receives a cylinder 80, freely slidable therein, to bear upon the cantilever arm 66 and damp vibrations thereof.

Turning to FIG. 5 for a moment, the cantilever arm 66 is illustrated as including an aperture 82. A jewel 86 includes a reduced portion 84 which extends through the aperture 82 to ride upon the upper surface of the film. The provision of a greater jewel dimension above the arm 66 prevents the jewel from being plucked from the arm by film defects. As illustrated in FIG. 5, the jewel 86 and the vane 64 may be secured to the arm 66 by a bonding material, such as epoxy or the like.

As set forth above, the recesses 46, 48 and 54 provide a space for the electrical leads 90, 92 and 94 and are covered by the plate 22 and an L-shaped cover 96. The cover 96 includes holes for receiving screws 98, 100 and 102 to secure the plate to the block 34 by threaded engagement in respective threaded bores 104, 106 and 108 in the block 34.

Referring to FIG. 6, the photocells 50 and 52 are illustrated in schematic form as photodiodes adjacent the lamp 44. Inasmuch as there are two identical channels, only one channel will be discussed in detail. The diode 50, for example, has a resistor 110 connected in parallel therewith and connected on one side to ground and on the other side to a capacitor 112 which is, in turn, connected to the (+) input of an operational amplifier 116. The amplifier 116 has a feedback resistor 118 connected between its output and its (−) input and is connected to the (+) input of a second amplifier 122 by way of a resistor 120. The amplifier 122 also has a feedback resistor 124 connected between its output 130 and its (−) input.

A dc supply is connected to a terminal 132 and supplies a constant voltage by way of a resistor 134 and a Zener diode 136. This constant voltage is applied to the lamp 44, to the (+) input of the amplifier 116 by way of a resistor 114 and to the (−) input of the amplifier 122 by way of an adjustable voltage divider including a resistor 126 and a resistor 128.

In operation, the light striking the diode 50 effects the generation of a dc voltage which is dependent upon the amount of light which, in turn, is dependent upon the modulation of the light by a vane. The changes in this dc signal are coupled to the amplifier 116 by way of the capacitor 112, amplified and fed to the amplifier 122. The amplifier 122 is provided with a response level by which the operator may reject signal changes of less than a desired magnitude. Signal changes of greater than the selected magnitude are amplified and utilized to operate the brake 16.

Satisfactory operation of a circuit constructed in accordance with FIG. 6 was found with a 50 VDC output of Fairchild rectifier 1205 and using LM 3900 integrated circuits and a 2.5 V, 28 ohm, 100 ma lamp. The other circuit components were:

| REFERENCE CHARACTER | VALUE |
| --- | --- |
| 110 | 100 ohm |
| 112 | 4 μf |
| 114 | 100 K |
| 118 | 100 K |
| 120 | 10 K |
| 124 | 100 K |
| 126 | 10 K |
| 128 | 10 K |
| 134 | 820 ohm |
| 136 | 12 volts |

Although the invention has been described by reference to a particular illustrative embodiment thereof, many changes and modifications of the invention may become apparent to those skilled in the art without departing from the spirit and scope of the invention. It is therefore intended that the patent warranted hereon include all such changes and modifications as may reasonably and properly be included within the scope of this contribution to the art.

What is claimed is:

1. A film inspection device for detecting flaws in motion picture film traveling over a film support, comprising:

a housing including a bore defining a light passageway and adapted to be mounted adjacent the film support;

a source of light mounted in said bore;

at least one light responsive element mounted in said bore to produce an output signal in accordance with the light received through the passageway from said source;

slot means defining a slot communicating with said bore; and cantilever vane means movably mounted on said housing to contact the surface of the film and extending through the slot in a light interference relationship between said source and said light responsive element.

2. The device of claim 1, wherein said light responsive element comprises a photocell.

3. The device of claim 1, wherein said vane means comprises a 1 mil thick metallized vane member.

4. The device of claim 1, wherein said vane means comprises a vane and a resilient arm mounting said vane.

5. The device of claim 4, comprising damping means in said housing to damp said resilient arm.

6. The device of claim 4, wherein said vane means comprises a jewel on said arm for contacting the traveling film.

7. The device of claim 6, wherein said arm includes an opening therein and said jewel includes a portion extending through the opening, and means securing said jewel to said arm.

8. The device of claim 1, comprising a pair of light responsive elements mounted in said bore including said one light responsive element, wherein said slot means defines a pair of slots communicating with said bore including the first mentioned slot, and wherein said source is mounted between said light responsive elements, and said cantilever vane means comprises a pair of vanes independently movably mounted and extending through respective slots between said source and respective ones of said light responsive elements and spaced apart to engage the surface of the film adjacent respective edges of the film.

9. Film inspection apparatus for detecting flaws in motion picture film, comprising:

a film support;

film moving means for moving the film across said film support, including braking means for stopping the film;

a braking circuit connected to operate said braking means; and a flaw detection device mounted adjacent said film support including a source of light, light modulating means comprising a cantilever arm and a jewel extending through and secured to said cantilever arm for contacting a surface of the moving film, and light responsive means connected to said braking circuit and operable to generate a braking signal to cause operation of said braking means in response to a flaw encountered by said light modulating means.

10. Film inspection apparatus according to claim 9, wherein said braking circuit comprises:

amplifier means having an adjustable operating level, said amplifier means connected to said braking means; and coupling means connecting said light responsive means to said amplifier means.

11. Film inspection apparatus according to claim 9, wherein said light modulating means comprises a pair of independently mounted light modulators for contacting the surface of the film adjacent opposite edges thereof, said light responsive means comprises a pair of photocells for receiving modulated light via respective ones of said modulators, and said braking circuit includes separate channels connected between respective ones of said photocells and said braking means to operate said braking means in response to flaws encountered at either edge of the film.

12. Film inspection apparatus according to claim 10, wherein said light responsive means produces a DC signal and said coupling means comprises a capacitor for coupling changes in the DC signal to said amplifier means.

13. Film inspection apparatus for detecting flaws in film, comprising:

a film support;

film moving means for moving the film across said film support, including braking means for stopping the film;

a braking connected to operate said braking means; and a flaw detection device mounted adjacent said film support including a source of light, light modulating means for contacting a surface of the moving film, and light responsive means connected to said braking circuit and operable to generate a braking signal to cause operation of said braking means in response to a flaw encountered by said light modulating means;

said braking circuit comprising amplifier means having an adjustable operating level, said amplifier means connected to said braking means and comprising first and second operational amplifier circuits connected in cascade and each including a feedback impedance, one of said operational amplifier circuits comprising a variable impedance connected to an input thereof for setting a response threshold at which braking will be effected, and coupling means connecting said light responsive means to said amplifier means.

14. A film inspection device for detecting flaws in motion picture film traveling over a film support, comprising:

a body adapted to be mounted above and adjacent the film support, said body including a first bore defining a light pssageway, a second bore intersecting said first bore, and a slot intersecting said first bore at a point spaced from said second bore;

a lamp mounted in said second bore on one side of said slot and extending into and directing a light beam through said first bore;

a photocell mounted in said first bore on the other side of said slot to receive the light beam and produce an electrical signal which is a function of the amount of light received;

a cantilever arm mounted on said body;

a jewel carried by said arm for contacting the upper surface of the film at a point above the film support, said arm including an aperture and said jewel including a reduced portion extending through said aperture to contact the film; and a vane carried by said arm and extending through said slot and into said first bore to vary the amount of light reaching said photocell in response to the surface profile of the film.

15. The device of claim 14, comprising:

a third bore in said body above said cantilever arm; and a damping member freely slidable in said third bore and bearing on said arm.

16. The device of claim 14, comprising:

a threaded bore in said body above said cantilever arm at a point adjacent its connection to said body; and a screw in said threaded bore for adjusting the loading on said arm.

17. The device of claim 14, wherein said lamp and said photocell include respective lead wires, and said body includes recesses in some of its surfaces to receive said lead wires, and comprising protective cover means releasably attached to said body to cover said recesses.

18. A film inspection device for detecting flaws in motion picture film which is traveling over a film support, comprising:

a substantially solid body adapted to be mounted adjacent the film support;

a cantilever arm secured to said body, said cantilever arm including an aperture;

a jewel including a reduced portion extending through said aperture to contact a surface of the film adjacent an edge thereof;

a pair of intersecting bores in said body and a slot in said body intersecting one of said bores;

a source of light extending through said one bore and into the other of said bores on one side of said slot;

a light detector mounted in said one bore on the opposite side of said slot; and a vane mounted on said cantilever arm and extending into said one bore through said slot in an interference relationship with the light from said source to provide signals at said light detector which are modulated in accordance with the edge condition of the film.

* * * * *